United States Patent
Lim et al.

(10) Patent No.: US 10,039,803 B2
(45) Date of Patent: Aug. 7, 2018

(54) OPHTHALMIC COMPOSITION COMPRISING CYCLOSPORINE AND TREHALOSE

(71) Applicant: HUONS CO., LTD., Gyeonggi-do (KR)

(72) Inventors: Jong Hwan Lim, Gyeonggi-do (KR); Sung-Woon Hong, Seoul (KR); Dae Woong Ko, Gyeonggi-do (KR); Seung Kwan Nam, Gyeonggi-do (KR); Mi Sun Ahn, Gyeonggi-do (KR); Deok-Kyu Hwang, Gyeonggi-do (KR); Yeong-Mok Kim, Seoul (KR); Key-An Um, Gyeonggi-do (KR)

(73) Assignee: HUONS CO., LTD., Gyeonggi-do (KR)

( * ) Notice: Subject to any disclaimer, the term of this patent is extended or adjusted under 35 U.S.C. 154(b) by 0 days.

(21) Appl. No.: 15/519,497

(22) PCT Filed: Oct. 19, 2015

(86) PCT No.: PCT/KR2015/011048
§ 371 (c)(1),
(2) Date: Apr. 14, 2017

(87) PCT Pub. No.: WO2016/060532
PCT Pub. Date: Apr. 21, 2016

(65) Prior Publication Data
US 2017/0224766 A1 Aug. 10, 2017

(30) Foreign Application Priority Data
Oct. 17, 2014 (KR) .................. 10-2014-0141089

(51) Int. Cl.
A61K 38/13 (2006.01)
A61K 47/26 (2006.01)
A61K 9/00 (2006.01)
A61K 9/107 (2006.01)

(52) U.S. Cl.
CPC ............ *A61K 38/13* (2013.01); *A61K 9/0048* (2013.01); *A61K 9/1075* (2013.01); *A61K 47/26* (2013.01)

(58) Field of Classification Search
CPC ......... A61K 38/13; A61K 47/26; C07K 7/645
See application file for complete search history.

(56) References Cited

U.S. PATENT DOCUMENTS

| | | | |
|---|---|---|---|
| 6,290,991 B1 * | 9/2001 | Roser .................. | A61K 9/0021 424/500 |
| 6,555,526 B2 | 4/2003 | Matsuo et al. ................ | 514/53 |
| 7,732,425 B2 | 6/2010 | Matsuo et al. ................ | 514/53 |
| 9,320,801 B2 * | 4/2016 | Wang .................. | A61K 38/13 |
| 2003/0186931 A1 | 10/2003 | Matsuo et al. ................ | 514/53 |
| 2014/0057854 A1 | 2/2014 | Mitra et al. ................ | 514/20.5 |
| 2015/0125494 A1 | 5/2015 | Wang et al. ........... | A61K 47/44 |
| 2016/0101050 A1 * | 4/2016 | Lee ................... | A61K 38/13 424/400 |
| 2016/0151457 A1 * | 6/2016 | Iadonato ............ | A61K 38/1767 514/20.8 |

FOREIGN PATENT DOCUMENTS

| | | | | |
|---|---|---|---|---|
| JP | 2002-161038 | 6/2002 | ......... | A61K 31/7016 |
| KR | 10-2002-0021320 | 3/2002 | ........... | A61K 31/715 |
| KR | 10-1211902 | 12/2012 | ........... | A61K 38/13 |
| KR | 10-2014-0054125 | 5/2014 | ............. | A61K 47/34 |
| WO | WO 2013-016494 | 1/2013 | ................ | A61J 1/00 |

OTHER PUBLICATIONS

International Search Report (ISR) dated Jan. 7, 2016 in PCT/KR2015/011048 published as WO 2016/060532.
Garweg, J.G., et al., (2006). "Effects of daunorubicin, mitomycin C, azathioprine and cyclosporin A on human retinal pigmented epithelial, corneal endothelial and conjunctival cell lines". *Graefe's Arch Clin Exp Ophthalmol* 244:382-389.
Lee, E., et al. (2007). "Effect of cyclosporine a 0.05% on human corneal epithelial cells, J Korean". *Ophthalmol Soc* 48(10):1399-1409.
Ji Eun Lee et al., Effect of Cyclosporine A 0.05% on Human Corneal Epithelial Cells, J Korean Ophthalmol Soc (2007) vol. 48, No. 10, pp. 1399-1409. (English abstract is on the last page, p. 1409).
Justus G. Garweg et al., Effects of daunorubicin, mitomycin C, azathioprine and cyclosporin A on human retinal pigmented epithelial, corneal endothelial and conjunctival cell lines, Graefe's Arch Clin Exp Ophthalmol (2006) vol. 244, pp. 382-389.
Kim et al., Comparative effectiveness of distilled water and isotonic saline in a rat model of dry eye, Journal of Biomedical Research (2010) vol. 11, No. 4, pp. 211-218.
Pauly et al., New tools for the evaluation of toxic ocular surface changes in the rat, Investigative Ophthalmology & Visual Science (2007), vol. 48, pp. 5473-5483.

* cited by examiner

*Primary Examiner* — Jeffrey E. Russel
(74) *Attorney, Agent, or Firm* — Harness, Dickey & Pierce, P.L.C.

(57) ABSTRACT

The present invention relates to an ophthalmic composition comprising cyclosporine and trehalose as effective components, a method for producing the same, a method for preventing, improving or treating failure caused by ophthalmoxerosis by administering the same, and a use therefor. The ophthalmic composition according to the present invention has a combination of superior effects on ophthalmoxerosis, which can be caused by various factors such as dry air, inflammation, preservatives, etc., and is placed in a variety of states or conditions.

13 Claims, 7 Drawing Sheets

OPHTHALMIC COMPOSITION COMPRISING CYCLOSPORINE AND TREHALOSE

CROSS-REFERENCE TO RELATED APPLICATIONS

This application is a national phase application of PCT Application No. PCT/KR2015/011048, filed on Oct. 19, 2015, which claims the benefit and priority to Korean Patent Application No. 10-2014-0141089, filed Oct. 17, 2014. The entire disclosures of the applications identified in this paragraph are incorporated herein by references.

FIELD

The present disclosure relates to an ophthalmic composition, a method for preparing the same, and a method for preventing or treating eye diseases.

BACKGROUND

The tears of the eye are made up of three layers, an oil layer, a water layer and a mucin layer, and the tear film has the three layered structure. Dry eye syndrome or dry eye diseases (hereinafter referred to as 'dry eye') come in a wide range of concepts, and in many cases, its cause is not known, and thus, dry eye is defined, rather than a disease, as an abnormal condition of eyes resulting from an unstable tear film caused by a decrease or change in quantity or quality of tears and the tear film breaking up faster than normal.

According to the definition, categories of dry eyes include diseases such as keratoconjunctivitis sicca, keratoconjunctival epithelial disorder, reduced lacrimal fluid secretion, Stevens-Johnson syndrome, dry eye syndrome, Sjögren's syndrome, tear deficiency, ocular hyperemia, tear film instability, or eye edema. Furthermore, categories of dry eyes include allergic conjunctivitis, viral conjunctivitis, or dry eyes after cataract surgery. Furthermore, recently, with the increasing number of contact lens wearers, spending time in artificial air-controlled environment, and opportunity to see visual display terminals (VDT) with the wide use of TVs and computers, factors that promote dry eyes drastically increased, and as a result, categories of dry eyes include contact lens wear-related dry eyes or VDT operation-related dry eyes.

Furthermore, those with dry eyes have, in many cases, disorder with keratoconjunctivitis sicca. Particularly, when there is a tear deficiency in in the mucus layer, corneal damage is serious, causing keratoconjunctival epithelial disorder, and categories of keratoconjunctival epithelial disorder include dry eyes, corneal epithelial defect, conjunctival epithelial defect, corneal epithelial erosion, reduced corneal thickness, corneal infiltrate, corneal perforation or corneal epithelial exfoliation, and the keratoconjunctival epithelial disorder results in corneal ulcer, keratitis, conjunctivitis, superficial punctate keratopathy, keratoconjunctivitis sicca, superior limbic keratoconjunctivitis, filamentary keratitis, corneal ulcer and infectious eye diseases of corneal and conjunctival epithelium. The keratoconjunctival epithelial disorder may be caused by injury in eye, microsurgery or hard contact lens wear.

Treatment of dry eyes focuses on allowing for the maintenance of at least a predetermined volume of tears by a conservative method such as replenishing artificial tear eye drops or blocking the lacriminal ducts temporarily or eternally, but recently, with the expansion of treatment concept, the trend of dry eye treatment moves toward active treatment using drugs which promote the secretion of lacrimal fluid even for mild dry eyes, rather than passive treatment for the purpose of syndrome alleviation. In keeping with this trend, the use of immunosuppressive agents to treat dry eyes becomes more frequent. The immunosuppressive agent includes cyclosporine, sirolimus, tacrolimus and their derivatives. Among them, one of the commercially available drugs is cyclosporine A 0.05% emulsion form eye drops (Restasis®). This is known as being effective in treating dry eye syndrome and its related keratoconjunctival epithelial disorder, but at the same time, is known as causing many side effects, and the most common abnormal reaction is burning sensation in eyes, and conjunctival hyperaemia, eye discharge, epiphora, eye pain, a foreign body sensation, pruritus, a sharp, stabbing sensation, vision impairment (often blurred vision) in some patients have been reported. According to the essay whose author is Ji Eun Lee et al., as a result of contact with 0.05% cyclosporine for 10 minutes, increased apoptosis and reduced cell viability was seen, and to use without toxic effect of corneal epithelial cells, the duration of exposure to 0.05% cyclosporine should be less than 10 minutes (J Korean Ophthalmol Soc 48(10):1399-1409, 2007), and cell viability significantly reduced at 0.05% (5 μg/mL) or more of cyclosporine (Graefe's Arch Clin Exp Ophthalmol (2006) 244: 382-389).

In addition to cyclosporine, the use of an excessive amount of immunosuppressive agents causes side effects such as anemia, leukopenia, thrombocytopenia, and hair loss. However, in keeping with the recent trend, for treatment of severe dry eyes as well as clinical symptoms of discomfort even in mild cases, immunosuppressive agents are actively used to treat dry eyes. Further, generally, patients with dry eyes have many drug types and frequent doses, and it is known that these factors reduce drug compliance and treatment effect.

On the other hand, trehalose is disaccharide in which two glucose molecules are joined together at their reducing residue, and has three optical isomers, a, α-trehalose, α, β-trehalose and β, β-trehalose. In the natural world, trehalose is present widely in bacteria, plants, and animals, and in the food industry, trehalose has a wide range of applications because of superior characteristics such as relatively low sweetness, anti-aging of starch and prevention of protein degradation during freezing/drying. Furthermore, Korean Patent Publication No. 10-2002-0021320 (published on Mar. 20, 2002) discloses wherein a composition containing trehalose as a sole active ingredient has an effect on the treatment of Sjögren syndrome.

However, there is no report about effects of an ophthalmic composition containing two ingredients, cyclosporine and trehalose, especially on the prevention, reduction, and further treatment of a wide range of dry eyes until now, and moreover, there is no review of a synergistic effect of the two ingredients when combined and the weight ratio or weight % range for showing the synergistic effect.

DISCLOSURE

Technical Problem

The problem to be solved by the present disclosure is to provide an ophthalmic composition that exerts an equivalent or superior effect with a reduced amount of cyclosporine, and has a superior combined effect on dry eyes that may occur via various channels and are put in various states or conditions, rather than a single disease.

Technical Solution

To achieve the object, the present disclosure provides an ophthalmic composition containing cyclosporine and trehalose, in which the two ingredients are mixed in a predetermined ratio or weight % range. The inventors found that this ophthalmic composition exerted an equivalent or superior effect with a reduced amount of cyclosporine, and had an effect that cannot be exerted by a composition containing cyclosporine alone or trehalose alone as an active ingredient, for example, a superior combined effect on dry eyes that may occur via various channels such as dry air, eye inflammation, or preservative and are put in various states or conditions, and gained the invention by preparing it as a cyclosporine-trehalose complex.

Therefore, the present disclosure provides an ophthalmic composition including cyclosporine and trehalose as active ingredients, a method for preparing the same, and a method for preventing, reducing or treating eye diseases (preferably, dry eyes) using the same.

More specifically, the present disclosure provides an ophthalmic composition including cyclosporine and trehalose as active ingredients, and preferably an ophthalmic composition for preventing, reducing or treating dry eyes.

Furthermore, the present disclosure provides a method for preventing, reducing or treating eye diseases (preferably, dry eyes) by administering an ophthalmic composition including a pharmaceutically effective amount of cyclosporine and trehalose to mammals (preferably, humans).

Furthermore, the present disclosure provides use of cyclosporine and trehalose for preparing an ophthalmic composition (preferably, an ophthalmic composition for preventing, reducing or treating dry eyes).

In the ophthalmic composition according to the present disclosure, when the two active ingredients are mixed at a predetermined ratio, a synergistic effect is produced and further, is maximized, and a weight ratio of cyclosporine: trehalose is preferably 1: 20-200, 1:20-190, 1:20-180, 1:20-170, 1:20-160, 1:20-150, 1:20-140, 1:20-130, 1:20-120, 1:20-110, 1:20-100, 1:20-90, 1:20-80, 1:20-70, 1:20-60, 1:20-50, 1:20-40, 1:20-30, 1:20, 1:30-200, 1:30-190, 1:30-180, 1:30-170, 1:30-160, 1:30-150, 1:30-140, 1:30-130, 1:30-120, 1:30-110, 1:30-100, 1:30-90, 1:30-80, 1:30-70, 1:30-60, 1:30-50, 1:30-40, 1:30, 1:40-200, 1:40-190, 1:40-180, 1:40-170, 1:40-160, 1:40-150, 1:40-140, 1:40-130, 1:40-120, 1:40-110, 1:40-100, 1:40-90, 1:40-80, 1:40-70, 1:40-60, 1:40-50, 1:40, 1:50-200, 1:50-190, 1:50-180, 1:50-170, 1:50-160, 1:50-150. When the weight ratio is less than 1:20, the combined effect on dry eyes that are put in various states or conditions cannot be expected, and when the weight ratio exceeds 1:200, it is impossible to maintain the effective osmotic pressure (about 230~320 mOsmol/kg) of eye drops, and to maintain transparent nano-emulsion.

Additionally, when the two active ingredients are mixed in a particular weight % range, a synergistic effect is produced, and further, is maximized, and cyclosporine is present at more than 0.01 weight % on the basis of the total weight of the ophthalmic composition. However, preferably cyclosporine is present at less than 0.1 weight %, and when cyclosporine is present at more than 0.1 weight %, there are side effects such as burning sensation and blurred vision. Preferably, cyclosporine is present at more than 0.01 weight % and less than or equal to 0.05 weight %, more than 0.01 weight % and less than 0.05 weight %, more than or equal to 0.02 weight % and less than or equal to 0.05 weight %, more than or equal to 0.02 weight % and less than 0.05 weight %, more than or equal to 0.02 weight % and less than or equal to 0.05 weight %, more than 0.01 weight % and less than or equal to 0.04 weight %, more than or equal to 0.02 weight % and less than or equal to 0.04 weight %, more than 0.01 weight % and less than or equal to 0.03 weight %, more than or equal to 0.02 weight % and less than or equal to 0.03 weight %, or 0.02 weight %, on the basis of the total weight of the ophthalmic composition.

Furthermore, trehalose may be present at more than or equal to 0.5 weight % on the basis of the total weight of the ophthalmic composition. For example, trehalose may be present at 0.5 weight % or more, 0.6 weight % or more, 0.7 weight % or more, 0.8 weight % or more, 0.9 weight % or more, 1 weight % or more, 1.1 weight % or more, 1.2 weight % or more, 1.3 weight % or more, 1.4 weight % or more, 1.5 weight % or more, 1.6 weight % or more, 1.7 weight % or more, 1.8 weight % or more, 1.9 weight % or more, 2 weight % or more, 2.1 weight % or more, 2.2 weight % or more, 2.3 weight % or more, 2.4 weight % or more, 2.5 weight % or more, 2.6 weight % or more, 2.7 weight % or more, 2.8 weight % or more, 2.9 weight % or more, 3 weight % or more, 3.1 weight % or more, 3.2 weight % or more, 3.3 weight % or more, 3.4 weight % or more, 3.5 weight % or more, 3.6 weight % or more, 3.7 weight % or more, 3.8 weight % or more, 3.9 weight % or more, 4 weight % or more, 4.1 weight % or more, 4.2 weight % or more, 4.3 weight % or more, 4.4 weight % or more, 4.5 weight % or more, 4.6 weight % or more, 4.7 weight % or more, 4.8 weight % or more, 4.8 weight % or more, 4.9 weight % or more, 5 weight % or more, 7.5 weight % or less, 0.5-7.5 weight %, 0.5-7 weight %, 0.5-6.5 weight %, 0.5-6 weight %, 0.5-5.5 weight %, 0.5-5 weight %, 0.5-4.5 weight %, 0.5-4 weight %, 0.5-3.5 weight %, 0.5-3 weight %, 0.6-7.5 weight %, 0.6-7 weight %, 0.6-6.5 weight %, 0.6-6 weight %, 0.6-5.5 weight %, 0.6-5 weight %, 0.6-4.5 weight %, 0.6-4 weight %, 0.6-3.5 weight %, 0.6-3 weight %, 0.7-7.5 weight %, 0.7-7 weight %, 0.7-6.5 weight %, 0.7-6 weight %, 0.7-5.5 weight %, 0.7-5 weight %, 0.7-4.5 weight %, 0.7-4 weight %, 0.7-3.5 weight %, 0.7-3 weight %, 0.8-7.5 weight %, 0.8-7 weight %, 0.8-6.5 weight %, 0.8-6 weight %, 0.8-5.5 weight %, 0.8-5 weight %, 0.8-4.5 weight %, 0.8-4 weight %, 0.8-3.5 weight %, 0.8-3 weight %, 0.9-7.5 weight %, 0.9-7 weight %, 0.9-6.5 weight %, 0.9-6 weight %, 0.9-5.5 weight %, 0.9-5 weight %, 0.9-4.5 weight %, 0.9-4 weight %, 0.9-3.5 weight %, 0.9-3 weight %, 1-7.5 weight %, 1-7 weight %, 1-6.5 weight %, 1-6 weight %, 1-5.5 weight %, 1-5 weight %, 1-4.5 weight %, 1-4 weight %, 1-3.5 weight %, 1-3 weight %, on the basis of the total weight of the ophthalmic composition. When trehalose is present at less than 0.5 weight %, the combined effect on dry eyes that are placed in various states or conditions cannot be expected, and when trehalose is present at more than 7.5 weight %, it is impossible to maintain the effective osmotic pressure (about 230~320 mOsmol/kg) of eye drops cannot be maintained, and to maintain transparent nano-emulsion.

For example, the ophthalmic composition may include more than 0.01 weight % and less than 0.1 weight % of cyclosporine and 0.5-7.5 weight % of trehalose, more than 0.01 weight %-less than 0.05 weight % of cyclosporine and 0.5-5 weight % of trehalose, more than 0.01 weight %-less than 0.05 weight % of cyclosporine and 0.5-3.5 weight % of trehalose, 0.02 weight % or more-less than 0.05 weight % of cyclosporine and 0.5-5 weight % of trehalose, 0.02 weight % or more-less than 0.05 weight % of cyclosporine and 0.5-3.5 weight % of trehalose, 0.02 weight % or more—less than 0.05 weight % of cyclosporine and 1-3 weight % of trehalose, 0.02 weight % of cyclosporine and 1-3 weight % of trehalose.

Preferably, for synergistic action of cyclosporine and trehalose, the ophthalmic composition according to the present disclosure preferably includes cyclosporine and trehalose within the aforesaid weight ratio or/and weight % range.

In the present disclosure, on the premise that the active ingredient of the same % on the basis of the total composition weight % is included in the ophthalmic composition as compared to an ophthalmic composition containing cyclosporine alone or trehalose alone as an active ingredient, the term "synergistic action" may include an enhanced or improved effect on the same disease exerted by the ophthalmic composition containing cyclosporine alone or trehalose alone as an active ingredient, an effect appearing on a disease that is not exerted by the ophthalmic composition containing cyclosporine alone or trehalose alone as an active ingredient, or an alleviated side effect or disadvantage involved in the ophthalmic composition containing cyclosporine alone or trehalose alone as an active ingredient. For example, the synergistic action may include a markedly increased treatment effect as compared to administration of cyclosporine alone or trehalose alone, effects on corneal damage reduction, recovery of the quantity of tear secretion, eye inflammation reduction, tear quality improvement, eye irritation (erythema, edema and increased discharge of conjunctiva) reduction, maintenance, lubrication and moisturizing of the tear film, and an effect in increasing the quantity of mucin secretion due to the goblet cell increasing activity in which goblet cells are responsible for the secretion of mucin, in all dry air-induced dry eye model, inflammation-induced dry eye model, and preservative-induced dry eye model.

In the present disclosure, "cyclosporine" or "trehalose" may be used irrespective of its preparation method and origin, so long as the object of the present disclosure is not hindered.

Furthermore, the cyclosporine may include, as its active substance, cyclosporine A, cyclosporine A derivatives, cyclosporine B, cyclosporine C, cyclosporine D and mixtures thereof, and preferably may include cyclosporine A. The trehalose may include, as its active substance, three optical isomers, α, α-trehalose, α, β-trehalose, β, β-trehalose and mixtures thereof.

Furthermore, in the present disclosure, the term "cyclosporine" or "trehalose" is defined as encompassing their pharmaceutically acceptable derivatives, and the pharmaceutically acceptable derivatives will be recognized as having or providing the same biological function and/or activity as cyclosporine or trehalose, and may include a prodrug of cyclosporine or trehalose, their solvate and their co-crystal, so long as the object of the present disclosure is not hindered.

The term "prodrug" refers to cyclosporine or trehalose formed in an amount that can be experimentally detected within a predetermined period of time through metabolism after administration.

The term "solvate" refers to a compound further including a stoichiometric or non-stoichiometric amount of solvents held by a non-covalent molecular force. In case that the solvent is water, the solvate is hydrate.

The term "co-crystal" refers to a crystalline form including at least one compound in a crystal lattice. The co-crystal includes a crystalline molecular complex of at least two non-volatile compounds held together in a crystal lattice through nonionic interaction. In the present disclosure, the co-crystal includes a pharmaceutical co-crystal which is a crystalline molecular complex including cyclosporine or trehalose, and at least one additional non-volatile compound (hereinafter referred to as counter-molecule). In the pharmaceutical co-crystal, the counter-molecule may be a non-toxic pharmaceutically acceptable molecule such as, for example, a food additive, a preservative, a medical excipient, or other APIs. In some embodiments, the pharmaceutical co-crystal improves some physical properties of drugs (for example, solubility, dissolution rate, biological availability/stability), while not degrading the chemical structural integrity of API.

Cyclosporine including its pharmaceutically acceptable derivatives and trehalose including its pharmaceutically acceptable derivatives may be prepared by a variety of chemical or enzymatic methods known in the art, or may be obtained from commercially available products.

The ophthalmic composition according to the present disclosure may be prepared by mixing the active ingredients, cyclosporine and trehalose.

The ophthalmic composition according to the present disclosure may be prepared as a pharmaceutical composition, a quasi-drug composition, and a health food composition.

The ophthalmic composition according to the present disclosure may include an additive such as a pharmaceutically (or sitologically) acceptable carrier, excipient or diluent, and the characteristics that must be taken into consideration for the additive include, but are not limited to, compatibility with cyclosporine and trehalose, biocompatibility, and processing temperature.

The ophthalmic composition according to the present disclosure may be prepared as a non-oral preparation such as an ophthalmic solution, an eye ointment, an injection and eyewash, or an oral preparation such as pills, capsules and granules, and a preferred administration type is an ophthalmic solution, and a most preferred administration type is eye drops.

In the case of being prepared as an ophthalmic solution, the ophthalmic solution may be provided in any administration type used for an ophthalmic solution, for example, an aqueous ophthalmic solution such as an aqueous ophthalmic solution, an aqueous emulsion ophthalmic solution, a viscous ophthalmic solution and a dissolved ophthalmic solution; or a non-aqueous ophthalmic solution such as a non-aqueous ophthalmic solution and a non-aqueous emulsion ophthalmic solution.

In the case of being prepared as an aqueous emulsion ophthalmic solution, the ophthalmic solution may include various additives known in the art, for example, a tonicity adjusting agent, a buffering agent, a stabilising agent, a pH adjusting agent, a thickening agent, a preservative, a chelating agent, a solubilizing agent and a solvent, so long as the object of the present disclosure is not hindered. The buffering agent may be selected from the group consisting of a phosphate buffering agent, a borate buffering agent, a citrate buffering agent, a tartrate buffering agent, an acetate buffering agent (for example, sodium acetate) tromethamine and amino acid, but is not limited thereto. Preferably, a phosphate buffering agent may be used. The tonicity adjusting agent may be selected from the group consisting of sugars such as sorbitol, glucose, erythritol and mannitol, polyhydric alcohols such as glycerin, polyethylene glycol and polypropylene glycol, and salts such as sodium chloride, but is not limited thereto. The preservative may be selected from the group consisting of benzalkonium chloride, benzethonium chloride, alkyl paraoxybenzoate such as methyl paraoxybenzoate and ethyl paraoxybenzoate, benzyl alcohol, phenethyl alcohol, sorbic acid and its salt, thimerosal, polyquaternium, benzododecinium bromide, oxychloro complex and chlorobutanol, but is not limited thereto. The stabilising agent may be selected from cyclodextrin and its derivatives, water-soluble polymer such as poly(vinylpyrrolidone), and surfactants such as polysorbate 80 (tween 80®), polysorbate 20 and tyloxapol, but is not limited thereto. The pH adjusting agent may be selected from the group consisting of hydrochloric acid, acetic acid, phosphoric acid, sulfuric acid, sodium hydroxide, potassium hydroxide, monoethanolamine, ammonia water and ammonium hydroxide, but is not limited thereto. The thickening agent may be selected from the group consisting of hydroxyethylcellulose, hydroxypropylcellulose, methylcellulose, hydroxypropylmethylcellulose and carboxymethylcellulose, polyvinylalcohol, carbomer, povidone, poloxamer, polycarbophil and its salt, but is not limited thereto. The chelating agent may be selected from the group consisting of sodium edetate, sodium citrate and condensed sodium phosphate, but is not limited thereto. The solubilizing agent or solvent may be selected from glycerin, DMSO, DMA, N-methylpyrrolidone, ethanol, benzylalcohol, isopropylalcohol, various molecular weights of polyethyleneglycol or propylene glycol, but is not limited thereto. There may be some overlaps between substances that can be used for the solvent or the solubilizing agent, and any substance may be used for any one of the solvent and the solubilizing agent, then if the substance acts as a solvent in the preparation, it is regarded as a solvent, and if the substance does not act as a solvent, it is regarded as a solubilizing agent. Alternatively, the solubilizing agent may be a surfactant in some variations. Surfactant combinations including various types of surfactants may be used. For example, nonionic, anionic (i.e., soap, sulfonate), cationic (i.e., CTAB), zwitterionic, polymeric, amphoteric surfactants may be used. For example, available surfactants include, but are not limited to, those having HLB of 10, 11, 12, 13, or 14 or more. Examples of surfactant include a polyoxyethylene product of hydrogenated vegetable oil, polyethoxylated castor oil or polyethoxylated hydrogenated castor oil, polyoxyl castor oil or its derivatives, polyoxyethylene-sorbitan-fatty acid ester, and polyoxyethylene castor oil derivatives, but is not limited thereto. According to a particular embodiment, the ophthalmic composition of the present disclosure may include more than 0.01 weight % and less than 0.1 weight % of cyclosporine, 0.5-7.5 weight % of trehalose, 1-10 weight % of a solubilizing agent, 0.01-2 weight % of a solvent, the remainder of a buffering agent and a tonicity adjusting agent, on the basis of the total weight of the composition.

The aqueous emulsion ophthalmic solution may be preferably prepared in a nano-emulsion type, and in this case, may include various additives known in the art, for example, oil and a surfactant, so long as the object of the present disclosure is not hindered. The oil includes at least one selected from the group consisting of propylene glycol monocaprylate, propylene glycol laurate, medium chain (C8~C10) triglycerides, glyceryl-1,3-dioleate, glyceryl monooleate, and glyceryl linoleate. The surfactant includes at least one selected from the group consisting of oleoyl macrogolglycerides, linoleoyl macrogolglycerides, caprylocaproyl polyoxylglycerides, polyoxyl 35 castor oil, polyoxyl 35 hydrogenated castor oil, polyoxyl 40 hydrogenated castor oil, polyoxyl 40 hydrogenated castor oil, a condensation product of ethylene oxide with 12-hydroxystearic acid, and polysorbate 80 (Croda, U.K.).

Most preferably, the aqueous emulsion ophthalmic solution may be prepared as transparent nano-emulsion type eye drops, and to prepare it, a reference may be made to, for example, Korean Patent Registration No. 10-0938500, but is not limited thereto.

The ophthalmic composition according to the present disclosure may be used for reducing, preventing or treating eye diseases, and preferably for reducing, preventing or treating disorder caused by dry eye.

The "disorder caused by dry eye" may include keratoconjunctivitis sicca, keratoconjunctival epithelial disorder, reduced lacrimal fluid secretion, Stevens-Johnson syndrome, dry eye syndrome, Sjögren's syndrome, tear deficiency, ocular hyperemia, tear film instability, or eye edema; allergic conjunctivitis, viral conjunctivitis, or dry eyes after cataract surgery; and contact lens wear-related dry eyes or VDT operation-related dry eyes.

Furthermore, the "keratoconjunctival epithelial disorder" may include dry eye, corneal epithelial defect, conjunctival epithelial defect, corneal epithelial erosion, reduced corneal thickness, corneal infiltrate, corneal perforation or corneal epithelial exfoliation; corneal ulcer, keratitis, conjunctivitis, superficial punctate keratopathy, keratoconjunctivitis sicca, superior limbic keratoconjunctivitis, filamentary keratitis, filamentary keratitis, corneal ulcer, and infectious eye diseases of corneal and conjunctival epithelium; keratoconjunctival epithelial disorder associated with injury in eye, microsurgery or hard contact lens wear.

In treatment and/or prevention of mammals, in particular, humans, dosage of the ophthalmic composition according to the present disclosure may be generally determined by those working in the medical industry or those having related ordinary skill. For example, when the composition according to the present disclosure is used as eye drops to an adult patient with dry eyes, a preferred dosage of the ophthalmic composition including cyclosporine and trehalose as active ingredients may be, for example, administration at a dose of 1~4 drops (about 0.025~0.1 mL) of eye drops including 0.02 weight % of cyclosporine and 1-3 weight % of trehalose 1~10 times per day, but is not limited thereto, and those working in the medical industry or those having related ordinary skill may determine a most optimal real dosage based on not only the age, weight, gender and reaction of a patient to treat, but also the condition that is expected with this treatment.

The ophthalmic composition according to the present disclosure may be filled and provided in a sterile container, and may be provided with instructions about its use, and the instructions may be mechanically attached to the container filled with the ophthalmic composition or a second container packaging the container, or may be packaged together in the second container.

Advantageous Effects

The ophthalmic composition according to the present disclosure containing cyclosporine and trehalose, in which the two ingredients are mixed in a predetermined ratio and/or a predetermined amount, has a superior combined effect on dry eyes that may occur via various channels such as dry air-induced, inflammation-induced and preservative-induced, and are put in various states or conditions. More specifically, the ophthalmic composition exerts an equivalent or superior effect with a reduced amount of cyclosporine. Additionally, than cyclosporine alone or trehalose alone, the ophthalmic composition produces a synergistic treatment effect much greater than when administered, and has effects on corneal damage reduction, recovery of the quantity of tear secretion, eye inflammation reduction, tear quality improvement, eye irritation (erythema, edema, and increased discharge of the conjunctiva) reduction, and maintenance, lubrication and moisturizing of the tear film, and particularly, has an effect in increasing the quantity of mucin secretion due to the goblet cell increasing activity in which goblet cells are responsible for the secretion of mucin.

BEST MODE FOR CARRYING OUT THE INVENTION

Figure 1:
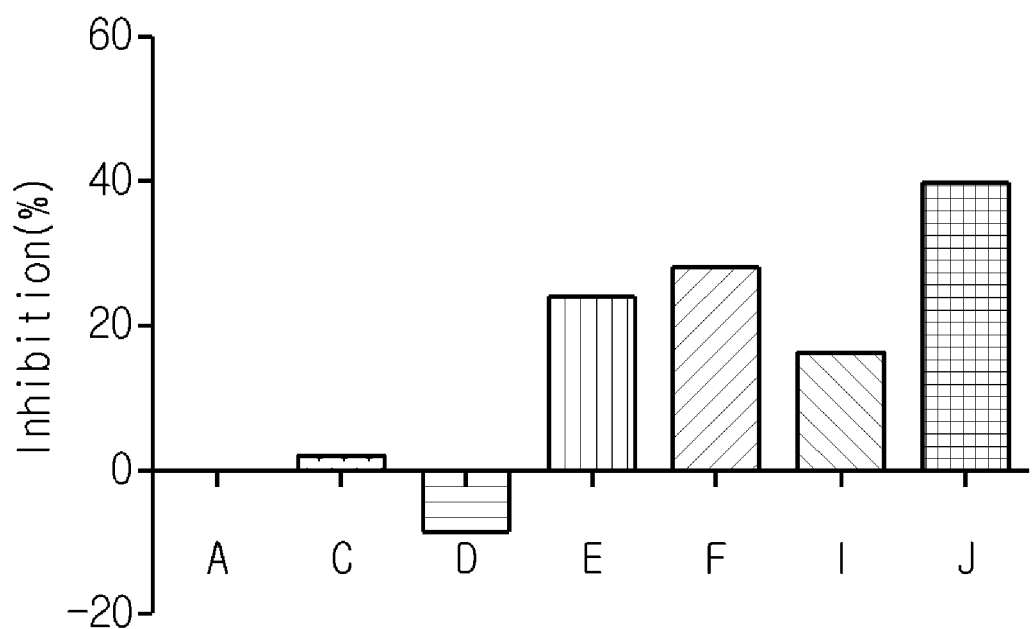
FIG. 1 shows changes of corneal damage inhibition in dry air-induced dry eye model treated with complex.

Hereinafter, the present disclosure will be described in more detail through examples. These examples are intended to describe the present disclosure in further detail and it is obvious to those skilled in the art that the scope of the present disclosure is not limited to the scope of disclosure of these examples.

Example 1. Preparation of Test Substance

According to each ingredient proportion of A to J in the following Table 1 (composition including cyclosporine A and trehalose at various concentration), cyclosporine was solubilized by mixing it with a solubilizing agent polyoxyl 35 castor oil. Glycerin was mixed with a phosphate buffer solution whose pH was set to 7.2 according to each proportion, and the solubilized cyclosporine solution was dispersed to prepare an emulsion. The osmotic pressure was adjusted to about 300 mOsmol/kg using trehalose and a tonicity adjusting agent in the prepared cyclosporine emulsion solution.

Test Example 1. Treatment Effect in Dry Air-Induced Dry Eye Model

Test Substance

The compositions A, C, D, E, F, I, J prepared according to example 1 described above were used as a test substance in the experiment.

Experimental Animal

The experimental animals, 6 week-old male Sprague-Dawley (SD) rats from Dae Han Bio Link Co. Ltd. (Eumseong, Chungbuk), were housed in cages for rats, each cage containing four rats. The animals were used in the experiment after acclimatization for about 1 week. The animal lab environment was controlled to Temperature 23±2° C., Relative humidity 55±10%, Frequency of ventilation 12 times/hour, Lighting cycle 12 hours, Illuminance 150-300 Lux. The palleted solid diet for experimental animals from Purina Rat Chow® Biopia Co., Ltd. (Gunpo, Gyeonggi) was fed, and the rats were allowed to freely drink sterile purified water.

Induction of Dry Eye and Treatment with Test Substance

20 μl of the test substance was applied to each of the two eyes of the experimental animal 30 minutes before exposure to air blower wind. In 30 minutes after applying to the eyes, 20 mg/kg of atropine (Sigma-Aldrich, St. Louis, Mo., USA) was administered into the abdominal cavity to inhibit tear secretion, and the animal was put under anesthesia by injecting Zoletil® (Virbac Korea, Seoul, Korea) into the muscles to maintain the uniform posture and control eye blinking. The anesthesized animal was fixed in front of the air blower to expose the two eyes squarely to the wind, and the distance was controlled to expose the eyes to air of 25-35% relative humidity at the wind speed of 2 m/sec. The test substance was applied repeatedly a total of ten times for 3 hours at the interval of 20 minutes from the time of exposure to dry air (0 minute), and after applying to the eyes, the eyelids were closed for about 10 seconds to spread the material over the eyes, and after then, the eyes were exposed to air. During the experimental period, the experimental animal was observed to prevent it from losing its posture or closing the eyes, and its posture was corrected frequently.

Measurement of the Extent of Corneal Damage

The extent of corneal damage was evaluated by the method of "Kim et al., (2010) Comparative effectiveness of distilled water and isotonic saline in a rat model of dry eyes. Journal of Biomedical Research 11(4):211-218". 5 μL of fluorescein (Sigma-Aldrich, St. Louis, Mo., USA) prepared at 1% in balanced saline solution (balanced sodium solution) was applied to the conjunctival sac of the animal in which dry eye was induced and to which the test substance was applied, and the animal was remained with eyes closed for 1 hour using a bandage. The residual dye that did not

TABLE 1

| Components | A | B | C | D | E | F | G | H | I | J |
|---|---|---|---|---|---|---|---|---|---|---|
| Cyclosporine A | 0 | 0.01% | 0.02% | 0.05% | 0 | 0 | 0.01% | 0.02% | 0.01% | 0.02% |
| Trehalose | 0 | 0 | 0 | 0 | 1% | 3% | 1% | 1% | 3% | 3% |
| Polyoxyl 35 castor oil | 3% | 3% | 3% | 3% | 3% | 3% | 3% | 3% | 3% | 3% |
| Ethanol | 0.1% | 0.1% | 0.1% | 0.1% | 0.1% | 0.1% | 0.1% | 0.1% | 0.1% | 0.1% |
| Glycerin | 0.8% | 0.8% | 0.8% | 0.8% | 0.8% | 0.8% | 0.8% | 0.8% | 0.8% | 0.8% |
| Phosphate buffer solution | Optimum | Optimum | Optimum | Optimum | Optimum | Optimum | Optimum | Optimum | Optimum | Optimum |
| Tonicity adjusting agent | Optimum | Optimum | Optimum | Optimum | Optimum | Optimum | Optimum | Optimum | Optimum | Optimum | permeate was washed with a saline solution, and the eye was enucleated. In the enucleated eye, a green fluorescent penetration region (area) of fluorescein penetrated into the cornea was observed under a tungsten lamp, and its photo was taken. The fluorescein penetration region was numerically indicated by analysis of the photo using Image J 1.38×program. To quantitate fluorescein permeated into the cornea, the resected cornea was deposited in potassium buffered saline (1 ml) and eluted for 24 hours, and then, the green fluorescent emission level (intensity) was evaluated by measuring fluorescence at excitation 485 nm, emission 538 nm using a fluorophotometer. When the corneal penetration and emission level of fluorescein is high, it signifies that the cornea has lost a barrier function, and thus, as the penetration and emission level is lower, the effect of the test substance is determined higher.

Pathological Test

After the test ended, all the experimental animals were killed by suffocation under carbon dioxide gas. The enucleated eye was fixed in Davidson solution for 7~24 hours, and fixed in 10% neutral formalin for at least 24 hours to prepare a tissue slice, followed by hematoxylin-eosin staining, and corneal epithelial damage and corneal thickness was measured under an optical microscope having a magnification of ×100. The conjunctival tissue resected at autopsy was fixed in 10% neutral formalin solution to prepare a tissue slice, followed by Periodic acid-Schiff staining (hereinafter, PAS staining), and the number of goblet cells containing or secreting mucin-like glycoproteins was counted under an optical microscope having a magnification of ×100.

Results

According to the experimental condition, dry eye is induced by a similar principle to dry eye caused by air conditioner or dry indoor air. For control group, the group treated with composition A prepared according to example 1 was used. The penetration region (area) (%) and emission level (intensity) (%) of the fluorescent stained cornea was calculated as a relative value when the penetration region (area)(%) and emission level (intensity)(%) of the fluorescent stained cornea of control group is each set to 100%.

Penetration region (area)(%) or emission level (intensity)(%)=[1−(control group−test group)/control group]*100

Corneal damage inhibition (%) was calculated by the following equation from the sum of averages of corneal penetration region (area)(%) and emission level (intensity) (%).

Corneal damage inhibition (%)=[(control group−test group)/control group]*100

Dry eyes induced by dry air for 3 hours greatly increased fluorescence intensity of corneal surface, and penetration of a fluorescent substance was found deep. The results were shown in FIG. 1, and it could be seen that corneal damage inhibition (%) of composition J corresponding to the complex according to the present disclosure amounted to about 40%. In contrast, it could be seen that composition (composition C and D) including cyclosporine A alone as an active ingredient had almost no effect on corneal damage treatment, and composition D had a deteriorating effect on corneal damage. Furthermore, composition (composition E, F) including trehalose alone as an active ingredient showed an effective effect on corneal damage, but showed an even lower preventive effect on corneal damage than that of composition J corresponding to the complex according to the present disclosure. In addition, in the case of composition I including both cyclosporine A and trehalose at a cyclosporine A:trehalose weight ratio of 1:300, the preventive effect on corneal damage was lower than that of a composition including trehalose alone. Furthermore, as a result of treating dry eyes caused by dry air with the test substance prepared according to example 1, it could be seen that the group treated with complex (composition J) of the present disclosure had a significant increase in the number of goblet cells containing or secreting mucin-like glycoproteins.

Test Example 2. Treatment Effect in Concanavalin A-Induced Dry Eye Model

Test Substance

The compositions A, B, C, D, E, F, G, H, J prepared according to example 1 described above were used as a test substance in the experiment.

Experimental Animal

The experimental animals, female New Zealand White (NZW) rabbits weighing 1.8-2.0 kg from Samtako Bio Korea (Osan, Gyeonggi), were housed in cages for rabbits, each cage containing one rabbit. The animals were used in the experiment after acclimatization for about 1 week.

The animal lab environment was controlled to Temperature 23±2° C., Relative humidity 55±10%, Frequency of ventilation 12 times/hour, Lighting cycle 12 hours, and Illuminance 150-300 Lux. The palleted solid diet for rabbits NIH#32M from Samtako Bio Korea was fed, and the rabbits were allowed to freely drink sterile purified water. The two eyes of the rabbit were examined 24 hours ahead of initiation of testing, and only animals having no eye damage such as corneal damage were used.

Concanavalin A and Treatment with Test Substance

After putting the experimental animal under anesthesia by injecting 50 mg/kg of Zoletil® and 6 mg/kg of xylazine into muscles, 50 μl of Concanavalin A (hereinafter, Con A) prepared at the concentration of 10 mg/ml in a physiological saline solution was injected into each of the main lacrimal gland and the accessory lacrimal gland of the upper eyelids of the two eyes using an insulin syringe (31-gauge needle). In 24 hours after Con A injection, each test substance was applied to the eyes for 3 days 4 times per day, and after applying to the eyes, the eyelids were closed for about 10 seconds so that the substance uniformly spreads over the eyes. General symptoms observation and imaging of the eyes was carried out once daily.

Measurement of Quantity of Tear Secretion (Schirmer Test)

To evaluate reductions in quantity of tear secretion, one side end of a cobalt chloride paper (Schirmer paper) was placed in the lateral canthus of the lower eyelid, causing tears to flow down to keep it wet for 30 seconds. When the quantity of tear secretion reduces, dry eye is promoted, so the effect of the test substance was determined to increase with the increasing quantity of secretion. The group treated with composition A prepared according to example 1 was used as control group.

Tear secretion inhibition (%)=[1−(test group−control group)/control group]*100

Determination of Extent of Corneal Staining and Inflammation

The extent of corneal staining and inflammation was determined by the method of "Pauly et al., (2007) New tools for the evaluation of toxic ocular surface changes in the rat. Investigative Ophthalmology & Visual Science."

The damaged part of the cornea was stained with fluorescein on the 4$^{th}$ day after applying the test substance to the eye, and the extent of fluorescein staining of each of the upper, middle and lower parts of the cornea was scored in accordance with the following criteria, and an average of the sum was calculated for each part.

(Determination Criteria)

0: not stained.

1: stained sparsely, each stained dot is apart from each other.

2: stained at intermediate density, some stained dots are close to each other.

3: stained densely, each stained dot is close to each other.

The group treated with composition A prepared according to example 1 was used as control group. The corneal inflammation alleviation (%) was calculated by substituting the average value of the sum of each part (upper, middle and lower parts of the cornea) obtained according to the determination criteria to the following equation:

Corneal inflammation alleviation (%)=(control group−test group)/control group*100

Pathological Test

At the 10$^{th}$ day after administration of the test substance, dry eye evaluation and eye irritation evaluation was conducted, and the rabbits were killed by suffocation under carbon dioxide gas. The cornea and conjunctival tissue resected at autopsy was fixed in 10% neutral formalin solution to prepare a tissue slice, followed by PAS staining, and the number of goblet cells containing or secreting mucin-like glycoproteins was counted under an optical microscope having a magnification of ×100.

Results

Figure 2:
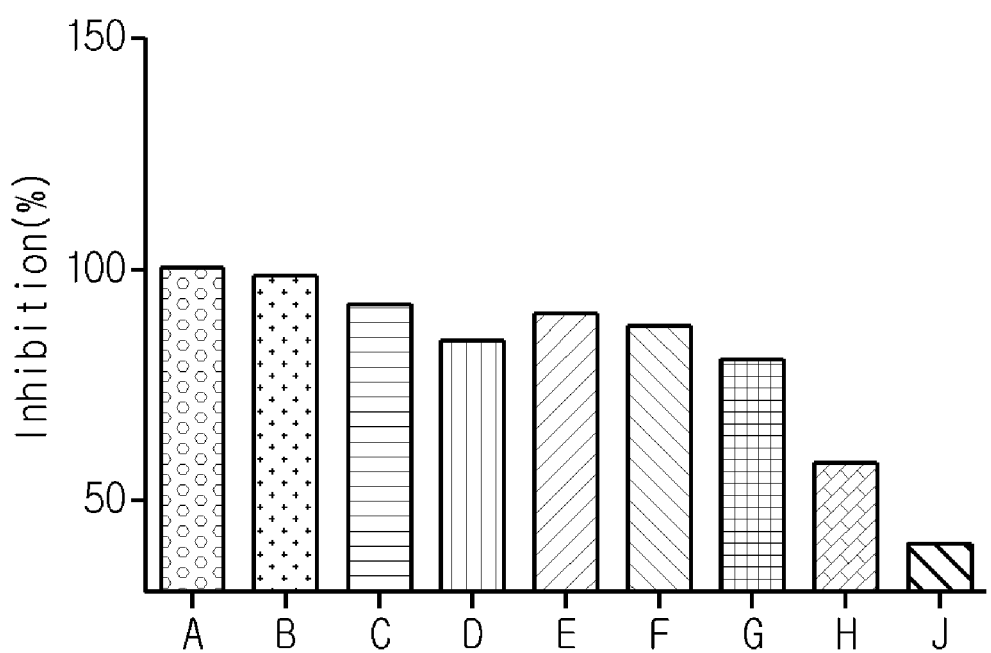
FIG. 2 shows changes of tear secretion inhibition in Concanavalin A-induced dry eye model treated with complex.
Figure 3:
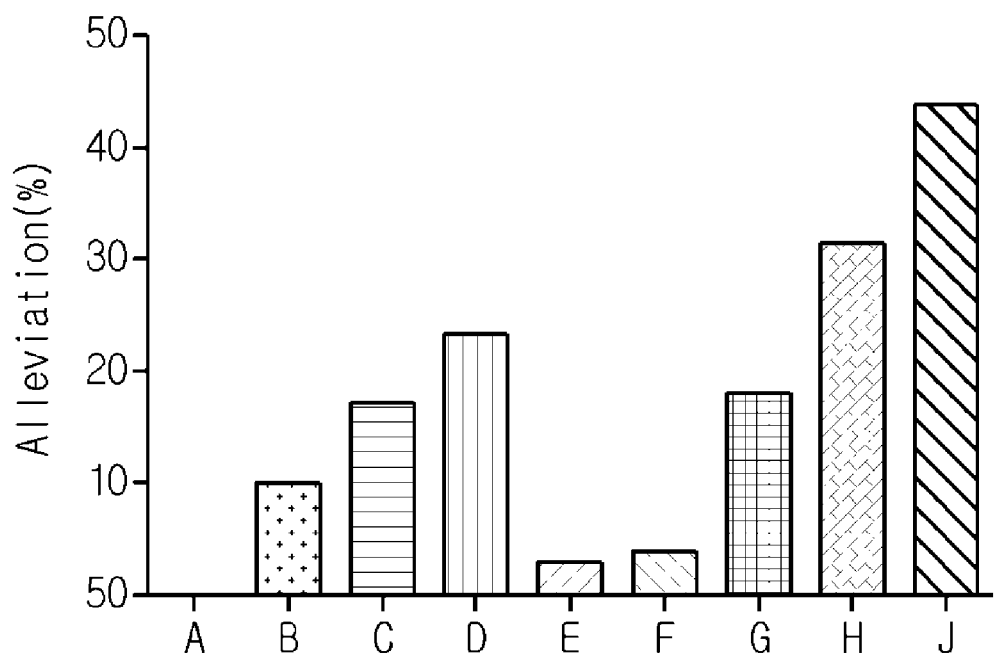
FIG. 3 shows changes of corneal inflammation alleviation in Concanavalin A-induced dry eye model treated with complex.

Con A, an inflammation inducing material, was administered to the lacrimal glands of rabbit, causing a reduction in quantity of tear secretion and corneal damage due to inflammation, and eye inflammation such as inflammation in the lacrimal glands. As a result of treating Con A-induced eye inflammation with the test substance prepared according to example 1, tear secretion inhibition (%) and corneal inflammation alleviation (%) was respectively shown in FIGS. 2 and 3.

As compared to the group treated with cyclosporine alone and the group treated with trehalose alone (composition B, C, D, E, F), the group treated with the complex (composition G, H, J) was found as having significantly increased in tear secretion. Contrary to the dry air-induced dry eye model, the group treated with trehalose alone (composition E, F) did not show inhibition of tear volume reduction caused by eye inflammation, and did not have an effect on the alleviation of corneal inflammation. Furthermore, the group treated with cyclosporine alone (composition B, C, D) had an effect on the alleviation of corneal inflammation, but did not show inhibition of tear volume reduction. In contrast, as a result of treatment with the complex (composition G, H, J) of the present disclosure, it could be seen that there was a synergistic effect in inflammation alleviation.

Furthermore, as a result of treating Con A-induced eye inflammation with the test substance prepared according to example 1, it could be seen that the number of goblet cells containing or secreting mucin-like glycoproteins significantly increased in the group treated with the inventive complex (composition G, H, J).

Test Example 3. Treatment Effect in Benzalkonium Chloride-Induced Dry Eye Model

Test Substance

The compositions A, D, J prepared according to example 1 described above were used as a test substance in the experiment.

Experimental Animal

The experimental animals, female New Zealand White (NZW) rabbits weighing 1.8-2.0 kg from Samtako Bio Korea (Osan, Gyeonggi) were housed in cages for rabbits, each case containing one rabbits. The animals were used in the experiment after acclimatization for about 1 week.

The animal lab environment was controlled to Temperature 23±2° C., Relative humidity 55±10%, Frequency of ventilation 12 times/hour, Lighting cycle 12 hours, and Illuminance 150-300 Lux. The palleted solid diet for rabbits NIH#32M from Samtako Bio Korea was fed, and the rabbits were allowed to freely drink sterile purified water. The two eyes of the rabbit were examined 24 hours ahead of initiation of testing, and only animals having no eye damage such as corneal damage were used.

Benzalkonium Chloride and Treatment with Test Substance

To induce dry eye, 100 µl of 0.1% Benzalkonium chloride (hereinafter, BAK) was administered into the conjunctival sac twice per day (9 am and 9 pm) for 15 days.

At the 5$^{th}$ day after BAK administration, whether dry eye was induced was determined by inspecting the tear break-up time (hereinafter, TBUT), the quantity of tear secretion, fluorescent staining and the degree of irritation, and dry eye induced rabbits were grouped by randomization. The test substance was administered twice per day (9 am and 9 pm) for 10 days from the 5$^{th}$ day after BAK administration.

The eyes were observed for general symptoms and abnormal reaction of the eyes once daily.

Evaluation of Dry Eye

Evaluation of dry eye (TBUT, quantity of tear secretion, fluorescent staining) was conducted before test substance administration (5$^{th}$ day after BAK administration), and 5 days (corresponding to the 10$^{th}$ day after BAK administration) and 10 days (corresponding to the 15$^{th}$ day after BAK administration) after test substance administration.

For TBUT, the time at which a fluorescent layer by fluorescein starts to break after applying 5 µl of fluorescein prepared at 0.1% to the conjunctival sac was measured under a slit lamp microscope. For TBUT, an average was obtained after three measurements.

For the quantity of tear secretion, one side end of a cobalt chloride paper (Schirmer paper) was placed in the lateral canthus of the lower eyelid, causing tears to flow down to keep it wet for 30 seconds, and the length was measured.

In fluorescent staining, the extent of corneal damage was determined by scoring the extent of fluorescein staining according to the following criteria for each of the upper, middle and lower parts of the cornea, and the extent of corneal damage was calculated from an average value of the sum scores of each part.

(Determination Criteria)

0: not stained.

1: stained sparsely, each stained dot is apart from each other.

2: stained at intermediate density, some stained dots are close to each other.

3: stained densely, each stained dot is close to each other.

Evaluation of Eye Irritation

Evaluation of eye lesion by test substance administration was conducted before test substance administration (5$^{th}$ day after BAK administration) and 5 days and 10 days after test substance administration, by measuring erythema, edema and discharge of the conjunctiva as follows. According to the following determination criteria, eye irritation results (erythema, conjunctival edema and discharge) were scored, and using an average value of them, eye irritation (%) was calculated. The eye irritation (%) was calculated based on average eye irritation score of composition A set to 100%.

Eye irritation (%)=(composition A irritancy−test substance irritancy)/composition A irritancy*100

Erythema (Palpebral conjunctiva and ocular conjunctiva only)
0: normal blood vessels
1: some blood vessels showing obvious signs of ocular hyperemia
2: wide crimson hue, respective blood vessels not observed easily
3: pale scarlet
Conjunctival Edema
0: not swollen
1: swollen a little more than normal (including nictitating membrane)
2: noticeably swollen, accompanied by partial outward movement of eyelid
3: swollen eyelid looking eye half closed
4: swollen eyelid looking eye closed more than halfway
Eye Discharge
0: no discharge
1: a slight amount of discharge (except a small amount observed at the inner corner of eye)
2: an amount of discharge that is large enough to wet eyelashes and eyelids
3: an amount of discharge that is large enough to wet a considerate area around eye, eyelashes, and eyelids
Pathological Test At the 10$^{th}$ day after test substance administration, evaluation of dry eye and evaluation of eye irritation was conducted, and after then all were killed by suffocation under carbon dioxide gas. The cornea and conjunctival tissue resected at autopsy was fixed in 10% neutral formalin solution to prepare a tissue slice, followed by PAS staining, and goblet cells containing or secreting mucin-like glycoproteins were observed under an optical microscope having a magnification of ×100.

Results

Figure 4:
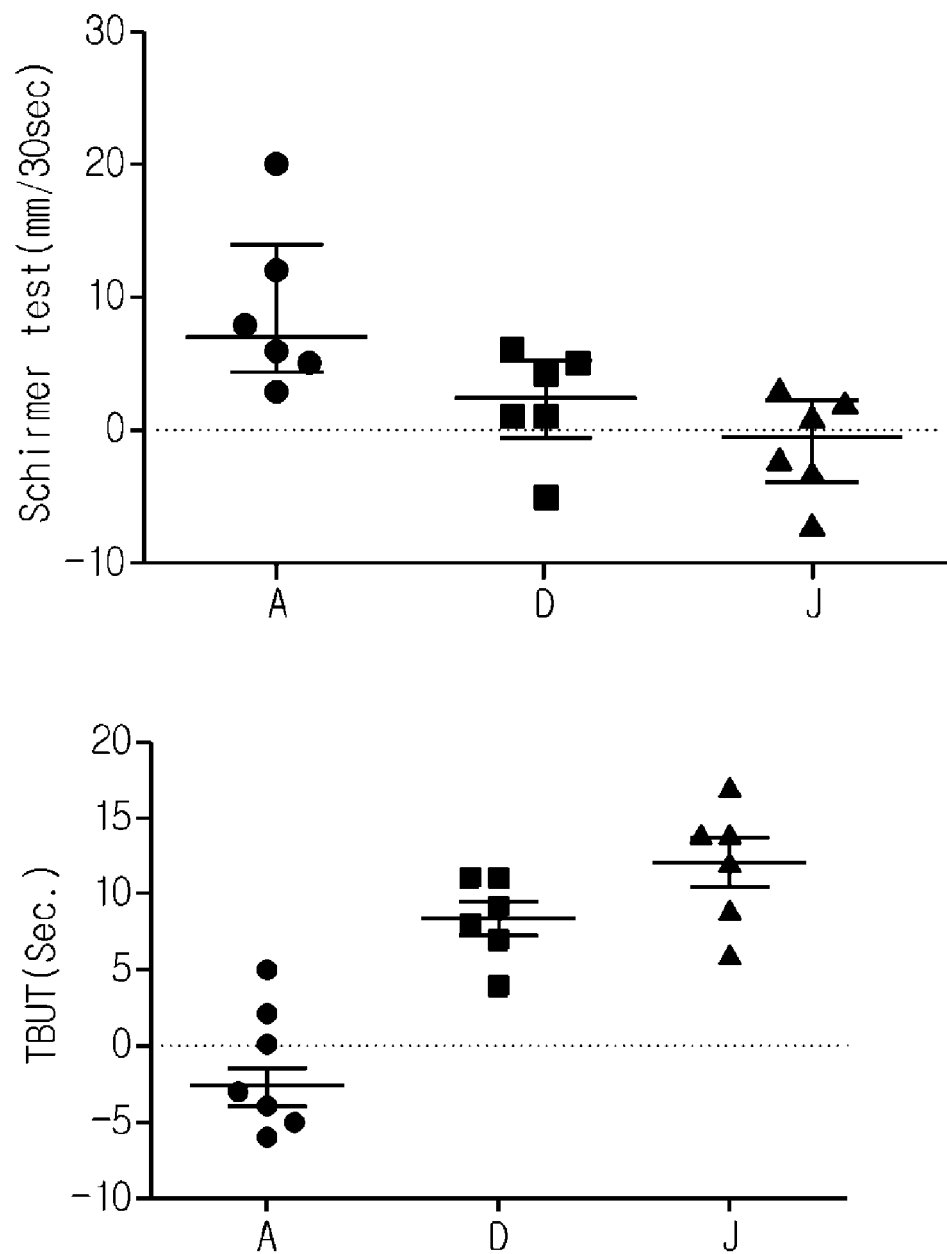
FIG. 4 shows Schirmer test changes (upper) and TBUT changes (lower) in Benzalkonium chloride-induced dry eye model treated with complex.
Figure 5:
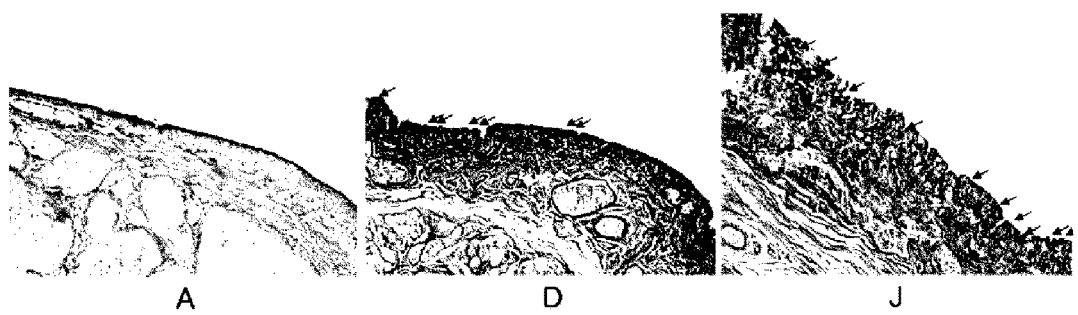
FIG. 5 shows the number of goblet cells in Benzalkonium chloride-induced dry eye model treated with complex.

BAK is a material widely used as a preservative and is being used as a preservative of liquid eye drops, but is a material known as causing dry eye when applied to eyes in excessive amounts. It is characterized by dry eye occurring by a different mechanism of action from Con A and dry air-induced dry eye models, and lesions lasting for a relatively long time. Dissimilar to other models, as symptoms develop, instability and premature break-up of the tear film occurs due to the increased amount of tears or reduced secretion of mucin-like glycoprotein, and potential damage of the corneal surface is accompanied by a combined factor of the surface of the eyeball, promoting dry eye. It could be seen that the group treated with complex (composition J) showed suppression of excessive tear secretion induced by BAK as compared to the group treated with cyclosporine A alone (composition D) (upper in FIG. 4), and inhibition of tear film breakup time shortening. It is well known that the shortened TBUT is the result of reductions in the mucin substance in the tear and the quantity of tear secretion (lower in FIG. 4). That is, in this experiment, treatment with the complex is expected to maintain the tear osmotic pressure through inhibition of excessive increase in amount of tears, and increase the quantity of mucin release (FIG. 5), leading to increased TBUT (lower in FIG. 4), as a result, improved quality of tear.

Figure 6:
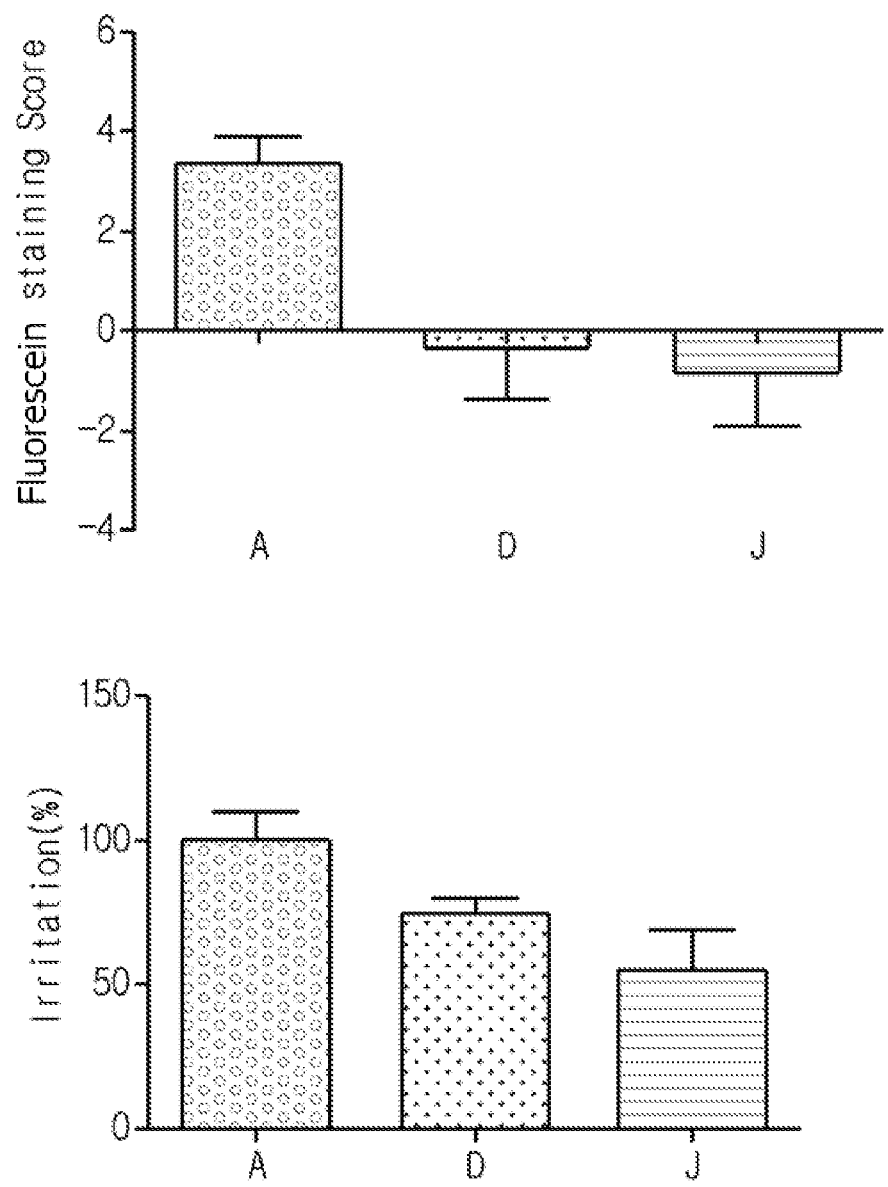
FIG. 6 shows changes in inflammation (upper) and the extent of eye irritation (lower) in Benzalkonium chloride-induced dry eye model treated with complex.
Figure 7:
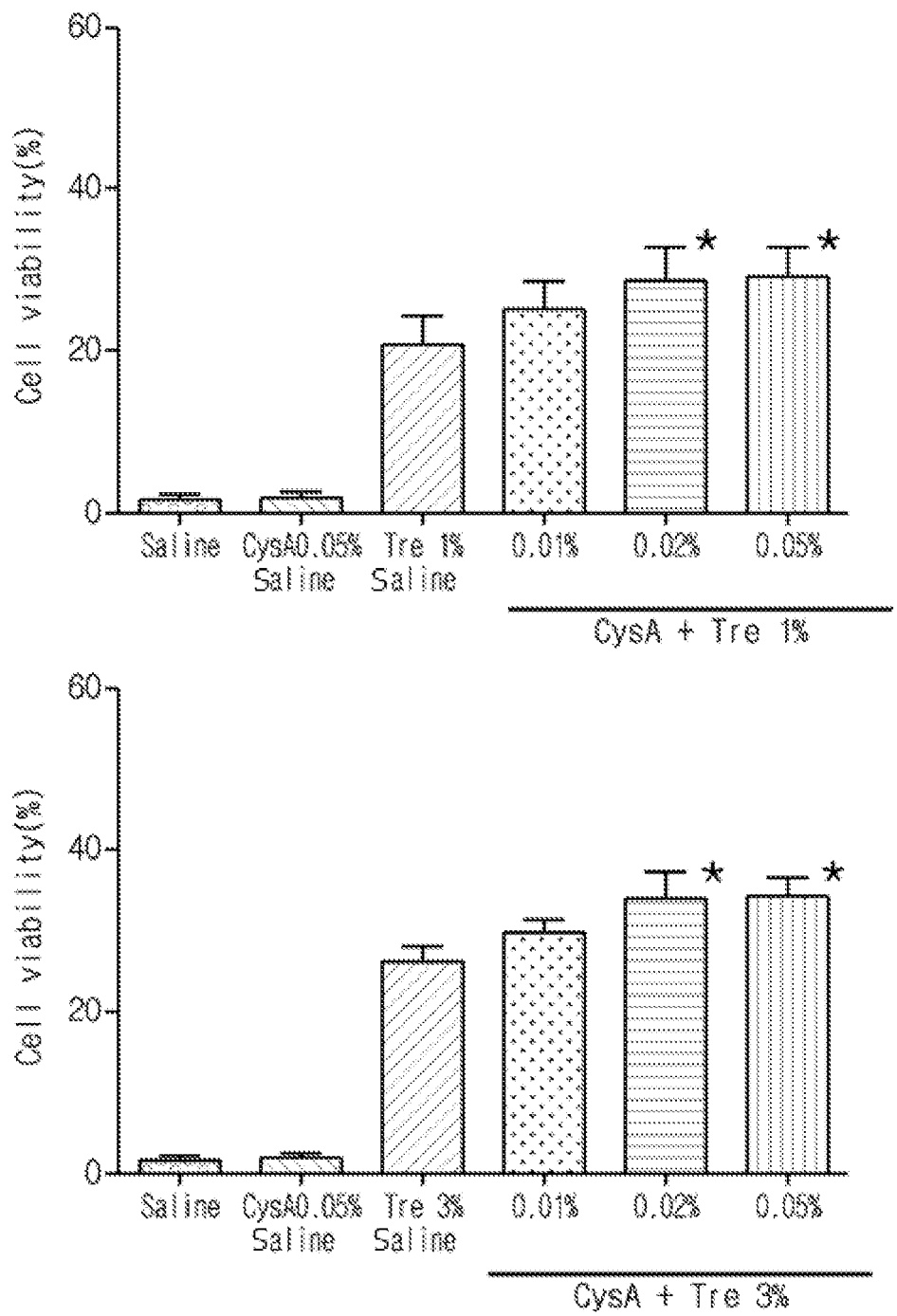
FIG. 7 shows cell viability in dry eye model treated with complex.

Furthermore, as a result of detecting the extent of corneal damage by fluorescent staining, it could be seen that the group treated with complex (composition J) was dramatically effective in healing corneal damage as compared to the group treated with cyclosporine A alone (composition D) (upper in FIG. 6).

Furthermore, the complex reduced inflammation caused by BAK treatment, and had an effect on the reduction of eye irritation (conjunctival injection and edema, increased discharge) appearing by BAK (lower in FIG. 6).

Example 2 and Test Example 4. Effect on Corneal Epithelial Cells in Dry Eye Model Test Substance The compositions A, D, E, F, G, H, I, J prepared according to example 1 described above were used as a test substance in the experiment. In addition, a composition including 0.05% of cyclosporine and 1% or 3% of trehalose was prepared according to example 1 and used in the experiment.

Cell Culture and Treatment

The corneal epithelial cells were cultivated in 37° C. culture medium, and the cell culture medium with 10% fetal bovine serum, epidermal growth factor, and antibiotics added to Dulbecco's Modified Eagle's Medium (DMEM, GibcoBRL, USA) was replaced at the interval of 2-3 days, and when the cells exhibited confluent growth, the culture medium was completely removed and washed with phosphate buffered saline (PBS) once, and then treated with 0.25% trypsin-EDTA to split the cells, which were used in the experiment.

Cell Viability Measurement

To evaluate cell viability of the corneal epithelial cells in dry environment, the corneal epithelial cells were washed with PBS once and contacted with the test substance for 10 minutes to remove the medicine, and the corneal epithelial cells were left under dry environment for 15 minutes. The medication was followed by cultivation for 18~24 hours, and cell viability was calculated by MTT method. Cell viability (%)=absorbance of each well/absorbance of control group well×100 was carried out three times for each concentration.

Test Results

All the test substances were each exposed to the corneal epithelial cells for 10 minutes, and exposed under dry environment for 15 minutes.

As a result, treatment with cyclosporine and trehalose together brought superior results in terms of viability of keratocytes as compared to the group treated with trehalose alone and the group treated with cyclosporine alone, and showed a definite increasing tendency based on the cyclosporine concentration. ($p<0.05$)

What is claimed is:

1. An ophthalmic composition comprising cyclosporine and trehalose as active ingredients, wherein a weight ratio of cyclosporine:trehalose is between 1:50 and 1:150, the cyclosporine is present at more than 0.01 weight % and less than 0.1 weight %, and the trehalose is present at 0.5 to 7.5 weight % based on the total composition.

2. The ophthalmic composition according to claim 1, wherein the cyclosporine is present at 0.02 to 0.05 weight %, and the trehalose is present at 1 to 3 weight %.

3. The ophthalmic composition according to claim 1, wherein the weight ratio of cyclosporine:trehalose is 1:50 or 1:150.

4. The ophthalmic composition according to claim 1, wherein the ophthalmic composition is for reducing, treating or preventing a disorder caused by dry eye.

5. The ophthalmic composition according to claim 4, wherein the disorder caused by dry eye is selected from the group consisting of keratoconjunctivitis sicca, keratoconjunctival epithelial disorder, reduced lacrimal fluid secretion, Stevens-Johnson syndrome, dry eye syndrome, Sjögren's syndrome, tear deficiency, ocular hyperemia, tear film instability, or eye edema; allergic conjunctivitis, viral conjunctivitis, or dry eye after cataract surgery; and contact lens wear-related dry eye or VDT operation-related dry eye.

6. The ophthalmic composition according to claim 5, wherein the keratoconjunctival epithelial disorder is selected from the group consisting of corneal epithelial defect, conjunctival epithelial defect, corneal epithelial erosion, reduced corneal thickness, corneal infiltrate, corneal perforation or corneal epithelial exfoliation; corneal ulcer, keratitis, conjunctivitis, superficial punctate keratopathy, keratoconjunctivitis sicca, superior limbic keratoconjunctivitis, filamentary keratitis, corneal ulcer and infectious eye diseases of corneal and conjunctival epithelium; and injury in eye, microsurgery or hard contact lens wear-related keratoconjunctival epithelial disorder.

7. The ophthalmic composition according to claim 1, wherein the ophthalmic composition is formulated as eye drops.

8. The ophthalmic composition according to claim 7, wherein the ophthalmic composition is transparent nano-emulsion type eye drops.

9. A method for preventing, reducing or treating a disorder caused by dry eye, comprising:
administering an ophthalmic composition including a pharmaceutically effective amount of cyclosporine and trehalose to a mammal,
wherein a weight ratio of cyclosporine:trehalose is between 1:50 and 1:150, the cyclosporine is present at more than 0.01 weight % and less than 0.1 weight %, and the trehalose is present at 0.5 to 7.5 weight % based on the total composition.

10. The method according to claim 9, wherein the disorder caused by dry eye is selected from the group consisting of keratoconjunctivitis sicca, keratoconjunctival epithelial disorder, reduced lacrimal fluid secretion, Stevens-Johnson syndrome, dry eye syndrome, Sjögren's syndrome, tear deficiency, ocular hyperemia, tear film instability, or eye edema; allergic conjunctivitis, viral conjunctivitis, or dry eye after cataract surgery; and contact lens wear-related dry eye or VDT operation-related dry eye.

11. The method according to claim 10, wherein the keratoconjunctival epithelial disorder is selected from the group consisting of corneal epithelial defect, conjunctival epithelial defect, corneal epithelial erosion, reduced corneal thickness, corneal infiltrate, corneal perforation or corneal epithelial exfoliation; corneal ulcer, keratitis, conjunctivitis, superficial punctate keratopathy, keratoconjunctivitis sicca, superior limbic keratoconjunctivitis, filamentary keratitis, corneal ulcer and infectious eye diseases of corneal and conjunctival epithelium; and injury in eye, microsurgery or hard contact lens wear-related keratoconjunctival epithelial disorder.

12. The method according to claim 9, wherein the cyclosporine is present at 0.02 to 0.05 weight %, and the trehalose is present at 1 to 3 weight %.

13. The method according to claim 9, wherein the weight ratio of cyclosporine:trehalose is 1:50 or 1:150.

* * * * *